US005641804A

United States Patent [19]
Breinholt et al.

[11] Patent Number: 5,641,804
[45] Date of Patent: Jun. 24, 1997

[54] FUNGICIDAL COMPOUND COMPRISING A CYCLIC POLYLACTONE

[75] Inventors: Jens Breinholt, Bagsvaerd; Ruby Ione Nielsen, Farum, both of Denmark

[73] Assignee: Novo Nordisk A/S, Bagsvaerd, Denmark

[21] Appl. No.: 392,879

[22] PCT Filed: Sep. 14, 1993

[86] PCT No.: PCT/DK93/00293

§ 371 Date: Mar. 3, 1995

§ 102(e) Date: Mar. 3, 1995

[87] PCT Pub. No.: WO94/06788

PCT Pub. Date: Mar. 31, 1994

[30] Foreign Application Priority Data

Sep. 15, 1992 [DK] Denmark ................................. 1134/92
Jun. 29, 1993 [DK] Denmark ................................. 0771/93

[51] Int. Cl.$^6$ ........................... C07D 323/00; C12P 1/02
[52] U.S. Cl. ................... 514/450; 549/267; 435/124; 504/140; 504/291; 504/117
[58] Field of Search ................. 549/450; 514/513; 435/124; 504/117, 140, 291

[56] References Cited

U.S. PATENT DOCUMENTS 3,836,544   9/1974   Urry et al. .......................... 549/267

OTHER PUBLICATIONS

Steinbuchler, Alexander, Nachr. Chem. Tech. Lab. 39 (1991), 1112 (SPEC).
JP Abstract 05,32658.
Ito et al., The Journal of Antibiotics, vol. 45, No. 10, pp. 1566–1572, (1992).
Ito et al., The Journal of Antibiotics, vol. 45, No. 10, pp. 1559–1565, (1992).
JP Abstract 03,262489.
Seuring et al., Chem, pp. 2044–2073, 1978.
P.A. Worthington, Natural Products Report, pp. 47–66, 1988.
Boeckman et al., Journal of American Chemical Society, pp. 5954–5957, 1974.
Fuska et al., The Journal of Antibiotics, vol. XXV, No. 4, pp. 208–211, 1972.
Seebach et al., Helvetica Chimica Acta, vol. 71, pp. 155–167, 1988.

*Primary Examiner*—Frederick Krass
*Attorney, Agent, or Firm*—Steve T. Zelson, Esq.; Cheryl H. Agris, Esq.

[57] ABSTRACT

The invention is directed to compounds having general formula (I) or general formula (II). Compounds of formulae (I) or (II) have interesting antifungal activities and may, accordingly, be used as active ingredients in fungicidal compositions.

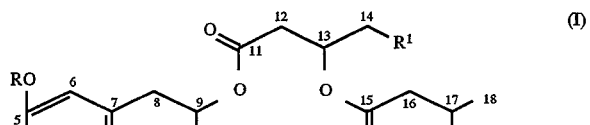

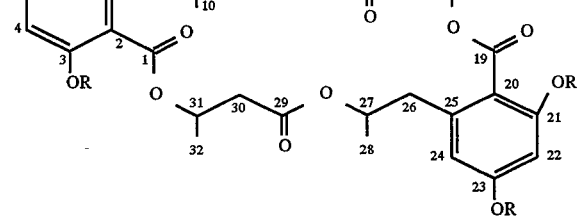

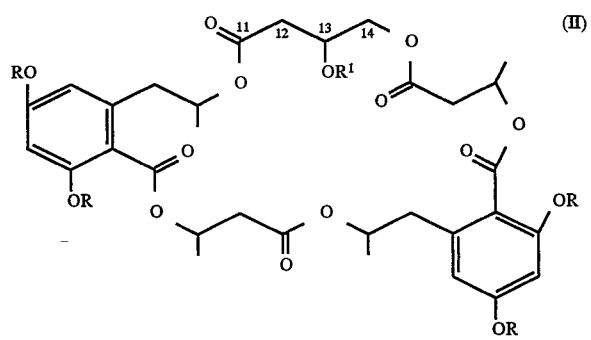

23 Claims, No Drawings

FUNGICIDAL COMPOUND COMPRISING A CYCLIC POLYLACTONE

CROSS-REFERENCE TO RELATED APPLICATIONS

This application is a continuation of PCT/DK93/00293 filed Sep. 14, 1993, which is incorporated herein by reference.

FIELD OF THE INVENTION

The present invention relates to biologically active compounds from microorganisms, including methods for the production and microorganisms capable of producing such compounds. The compounds of this invention are novel macrocyclic polylactones, composed of hydroxylated aromatic acids and aliphatic β-hydroxy acids and showing interesting biological activities against various fungi.

BACKGROUND OF THE INVENTION

It is well known that some microorganisms are capable of producing metabolites showing interesting biological activities. Such compounds are of potential interest for use in various fields, such as medicine, agriculture, food industry etc.

In the agricultural field biocidal microbial metabolites are considered to be highly interesting alternatives to the synthetic and, from an environmental point of view, generally undesirable compounds normally used for controlling diseases and pests in valuable crops. Accordingly, a fair amount of research has been devoted to the identification and development of such metabolites, which research to date, however, has resulted in only few useful biological (i.e. metabolite based) biocides as compared to the vast number of synthetical biocides presently used. It is consequently desirable to find further microbial metabolites useful as biocidal agents.

Hydroxyalkanoic acids are commonly occurring metabolites in various organisms. Polymerics forms of these, and especially poly β-hydroxybutyric acids, typically composed of several hundreds of units, occur in many bacteria as storage material, with the same function as starch and glycogen in higher organisms (Steinbüchel (1991)). Cyclic oligomers, being somewhat related to the compounds of the present invention, have also been described (Seebach et al. (1988)), but apparently no biological activity has been associated with these compounds.

The genus Penicillium is known to be an efficient producer of secondary metabolites having a diversity of structural features. One group of secondary metabolites encountered in said genus is macrocyclic lactones or the macrolides. An example from this group is the 16-membered dilactone vermiculin (P. vermiculatum) which exhibits antimicrobial effects (Fuska et al. (1972)), (Sedmera et al. (1973)), (Boeckman et al (1974)).

JP-A-3-262489 discloses a metabolite termed NG-012 produced by and isolated from a strain of Penicillium verruculosum F-4542. NG-012 was reported as a nerve growth factor potentiator, and no further activity of this compound was described or indicated. No mention or indication of the structure of NG-012 was given in the above cited Japanese application. The structure of this compound was reported only after the filing date of the present application, cf. the disclosure of Mayumi Ito et al., October 1992.

SUMMARY OF THE INVENTION

It has now surprisingly been found that novel macrocyclic polylactones structurally related to the above mentioned NG-012 and produced by the fungal genus Penicillium have interesting fungicidal activities. The present invention relates to such macrocyclic polylactones as well as their use as antifungal agents.

More specifically, in its first aspect the present invention relates to a group of novel macrocyclic polylactones composed of aliphatic β-hydroxy acids and hydroxylated aromatic acids, having the general formula I,

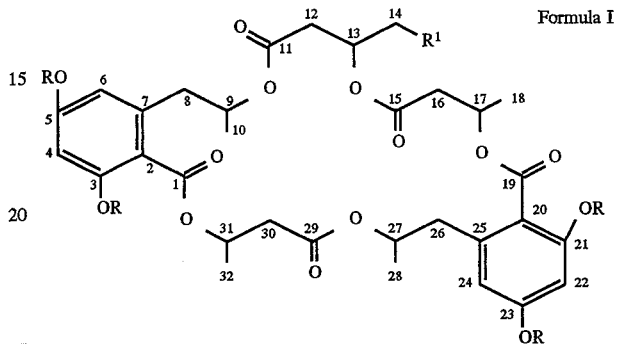

Formula I wherein $R^1$ is hydrogen, hydroxy, —$OR^2$, or —$OCOR^3$, in which $R^2$ is straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group; and $R^3$ is straight or branched alkyl with 1–10 carbon atoms, straight or branched alkenyl with 2–10 carbon atoms, straight or branched alkynyl with 2–10 carbon atoms, or aryl, optionally mono- or plurisubstituted with straight or branched alkyl with 1–10 carbon atoms, hydroxy, alkoxy, halogen, an amino or a nitro group; and R is hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group, or —$COR^3$ in which $R^3$ is as defined above.

In a second aspect, the present invention relates to a compound having the general formula II,

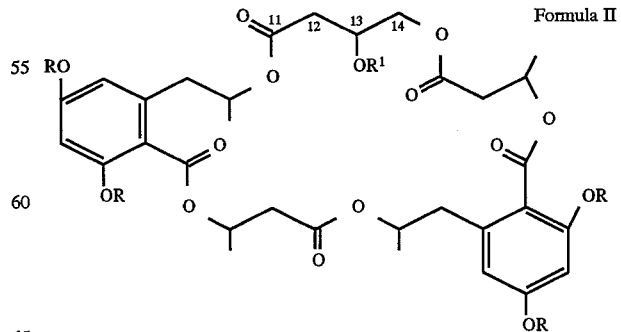

Formula II wherein R and $R^1$ independently are hydrogen, straight or branched alkyl with 1–10 carbon atoms, straight or branched. alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group, or —$COR^3$ where $R^3$ is as defined above for compounds of formula I.

Compounds of formula I and II are obtainable as natural or chemically modified metabolites from microorganisms such as a fungi, especially from a fungus of the genus Penicillium. The compounds have surprisingly been found to exhibit growth inhibiting activity against plant pathogenic fungi, and are therefore of particular interest as constituents in antifungal compositions.

In a third aspect the invention relates to a process for the production of compounds of the invention, which either involves cultivation of specific microorganisms capable of producing the compounds or chemical processes for full or semi-synthetic production of the compounds.

In a further aspect the present invention relates to a fungicidal composition comprising, as an active ingredient, one or more of the novel compounds of the invention or, alternatively, a microorganism capable of producing such compounds. Further constituents of the composition are suitable excipients, such as diluents, carriers etc. and optionally, if desired, other biocidal and/or growth-promoting compounds.

In a further aspect the invention relates to a method of controlling fungi at a locus infested or liable to be infested therewith, which comprises applying to said locus an antifungal composition as defined above of the invention.

In a still further aspect, the invention relates to the use of the novel compounds for controlling plant diseases, especially fungal attack, and as preservatives and/or additives to control fungi in foods and feeds, timber and wood, paints, growth media, cosmetics etc. Also, within the invention is the use of a microorganism capable of producing a compound of the invention for biological control such as for foliar, soil or seed application.

Finally, the invention relates to an isolated pure culture of the microorganism *Penicillium verruculosum* (IMI 352119) or a mutant thereof capable of producing a compound of the invention. Said microorganism was previously supposed to belong to the species *Penicillium aculeatum*.

In the present context, the term "mutant" is intended to indicate any organism derived from the *P. verruculosum* sp. of the invention which has retained the capability of producing a compound of the invention having either formula I or formula II. The mutant may be a natural mutant or one which is obtained by a synthetic process, e.g. by subjecting a culture of the microorganism of the invention to a mutagenesis treatment as known in the art.

DETAILED DESCRIPTION OF THE INVENTION

The compounds of the invention of (formulae I and II) belongs to a large and wide spread group of secondary metabolites, the macrocyclic lactones or macrolides. They can be grouped according to the ring size and to the number of ester linkages in the ring (monolactones, dilactones etc.). The compounds of formula I and II are 24- and 25-membered, respectively, pentalactones being unique in having aromatic hydroxy acids incorporated in the ring structure. As mentioned above some macrolides have been reported from Penicillium sp, but the majority has been isolated from Streptomyces sp. The macrolides include the polyenes of which a vast number has been described. They are polyhydroxylated macrolides with a characteristic polyene chromophore incorporated in the ring. Some have shown interesting activities against various plant pathogens (Worthington (1988)). Another group with interesting biological activities, also produced by Streptomyces sp., comprises the 16-membered unsaturated macrolides, including hygrolidins.

Being macrocyclic ring structures some of the macrolides are supposed to be capable of forming cages, which can trap ions of a suitable size and charge. In this way they can act as ionophores and disturb the balance of vital ions across membranes.

In connection with the compounds of the present invention having the formula I and II, respectively, the term "alkyl with 1–10 carbon atoms" is intended to include methyl, ethyl, propyl, butyl, pentyl, hexyl etc. straight, branched or cyclic where appropriate.

The term "alkenyl with 2–10 carbon atoms" is intended to include ethenyl, propenyl, butenyl, pentenyl, hexenyl etc. straight, branched or cyclic where appropriate. Also polyenyl (dienyl, trienyl etc.) is intended to be included in the term.

The term "alkynyl with 2–10 carbon atoms" is intended to include ethynyl, propynyl, butynyl pentynyl, hexynyl etc. straight, branched or cyclic where appropriate. Also polyynyl (diynyl, triynyl etc.) is intended to be included in the term.

The term "aryl" is intended to include aromatic radicals like phenyl, naphtyl, phenantryl etc. and hetero aromatic radicals like furanyl, thiophenyl, pyridinyl, imidazolyl, oxazolyl etc.

The term "plurisubstituted" covers di-, tri-, tetra- or higher substitution.

The term "halogen" covers fluorine, chlorine, bromine and iodine.

Preferred compounds of formula I are those in which R is methyl and/or $R^1$ is hydrogen or hydroxy, and in which R is —$COCH_3$ and/or $R^1$ is hydrogen, hydroxy or —$OCOCH_3$. The chiral centers of any of these compounds may indepently be in the (R)- or (S)-configuration.

A specifically preferred compound of formula I is one, in which R and $R^1$ both are hydrogen and, the chiral centers independently are in the (R)- or (S)-configuration. This compound is termed compound Ib in the following.

Another specifically preferred compound of formula I is one in which R is hydrogen and $R^1$ is hydroxy and, the chiral centers independently are in the (R)- or (S)-configuration. This compound is termed compound Ia in the following.

Examples of preferred compounds of formula II are those, in which R is hydrogen or methyl and/or $R^1$ is hydrogen or $COCH_3$. The chiral centers of any of these compounds may independently be in the (R)- or (S)-configuration.

A specifically preferred compound is one in which R and $R^1$ are hydrogen and the chiral centers independently are in the (R)- or (S)-configuration. This compound is termed compound IIa in the following.

It has been found that the absolute configuration of the aromatic acid residues (C-9 and C-27) of compounds Ia, Ib and IIa is R. The configuration of the β-hydroxy acid residues (C-13, C-17 and C-31) has been found to be R, except for C-13 in Ia and IIa, which are S. However, the absolute configuration of these β-hydroxy acid residues, whether R or S, might not have any substantial impact on the biological activity of the compounds. This is based on observations made for vermiculine and pyrenophorin, both macrolides produced by Penicillium sp., for which different optical isomers have been synthetized and no significant differences in biological activities were observed (Seuring and Seebach (1978)).

Accordingly, the absolute configuration of the aromatic acid residues and the β-hydroxy acid residues of formula I and II of the invention may be R or S.

In a further aspect the present invention relates to a method of preparing a compound of the invention as defined above, comprising a) cultivating a microorganism capable of producing said compound in or on a suitable nutrient medium and under suitable conditions so as to obtain a biomass comprising the compound, and b) recovering the compound from the biomass and/or the culture medium.

The microorganism which is capable of producing compounds of the invention is normally a fungus, preferably a fungus of the genus Penicillium, and more preferably a fungus of the species *P. verruculosum*, in particular the strain thereof identified by the deposition number IMI CC 352119, or a mutant of said strain capable of producing a compound of the invention.

A suitable nutrient medium is one which comprises the micro-and macronutrients required to obtain a satisfactory growth of the microorganism in question and at the same time give rise to a sufficient production of the compound of the invention when subjected to suitable cultivation conditions.

Normally, a suitable nutrient medium contain sources of carbon and nitrogen assimilable by the microorganism and normally a low level of inorganic salts. In addition, the nutrient medium may contain traces of metals and other components necessary for the growth of the microorganisms and the production of the desired compound. Such other components may be in sufficient concentrations in the complex sources of carbon and nitrogen, typically used as nutrient sources, but can, of course, be added separately to the medium if desired.

The conditions under which the microorganism is cultivated may be chosen so as to optimize the production of secondary metabolites therefrom. The optimization of the production of secondary metabolites may be performed by methods known in the art, such as methods based on batch fermentation, fed-batch fermentation or continuous fermentation.

The compound produced may be contained in the biomass or may alternatively be excreted into the culture medium, fully or partially, depending on the microorganism in question. In the case of a fungus, such as a fungus of the species Penicillium, especially the *Penicillium verruculosum* identified by the deposition number (IMI 352119), the compound is normally contained in the biomass, such as in or on the mycelium the spores and the like.

The recovery of the compound of the invention from the bio-mass and/or culture medium produced in accordance with step a) above may be performed by any suitable technique useful for the microorganism in question. When the compound is contained in the biomass, e.g. a fungal mycelium, the recovery comprises harvesting the mycelium, e.g. by filtration and/or centrifugation, and subsequently isolating the compound therefrom. Suitable methods for isolating the compound includes extraction using a suitable solvent such as methanol, ethanol, ethyl acetate, or acetone, and solid phase extraction using a hydrophobic resin, an example of which is XAD-8 (Rohm and Haas Co.). Further purification may be accomplished by chromatography and/or crystallisation.

In order to improve certain properties of the metabolite such as its solubility in aqueous media, its hydrophobicity, hydrophilicity, stability, specificity, toxicity, target spectrum, potency, UV or heat resistance or the sensitivity of the compound to pH variations, etc. as well as membrane permeability and translocation of the compound in the host plant to which it is applied, it may be advantageous to subject the isolated natural metabolite to a chemical modification. Alternatively, modification may be achieved by feeding suitable precursors to the medium in which the microorganism producing the compound is cultured, so as to obtain production of the derivative, or by subjecting the microorganism or its genetic material to genetic modification in accordance with well-known technology. Furthermore, derivatives may be produced by chemical synthesis using the natural metabolite as a lead structure. The compounds produced by such modifications may either belong to the group of compounds having the general formula I or II or may be different from these compounds.

Specific examples of the production of compounds of formula I or II are given in the examples below, in which the production of the compounds Ia, IIa and Ib from a strain of the deposited microorganism of the invention is described.

While it is contemplated that compounds of the invention having formula I or formula II may be prepared by the general method outlined above, i.e. from a microorganism capable of producing such compounds, some compounds of the invention may advantageously be prepared from the compounds Ia, Ib or IIa using a synthetic process.

Thus, ester derivatives of the compounds Ia, Ib or IIa being compounds of formula I or II, respectively (wherein $R^1$ is $-OCOR^3$ in formula I and $R^1$ is $-COR^3$ in formula II) may be prepared by treating the compounds Ia, Ib or IIa, respectively, dissolved in a suitable solvent with appropriate acylating reagents such as acid halides, acid anhydrides or activated esters, optionally under influence of a basic catalyst (pyridine, other amines etc.). Ether derivatives of the compounds Ia, Ib or IIa (wherein $R^1$ is $-OR^2$ in formula I and $R^1$ is $R^2$ in formula II) may be prepared by treating the compounds Ia, Ib or IIa, respectively, dissolved in a suitable solvent with an appropriate alkylating reagent, such as a diazo compound. Alternatively, appropriate alkyl halides and the like, under influence of a catalyst (potassium carbonate, silver oxide etc.) may be used as alkylating reagent, and the reaction performed in a suitable solvent like acetone, dimethylformamide etc.

It is also contemplated that compounds according to the invention whether of formula I or II, may be produced entirely by well known chemical synthetic processes using available starting materials.

The compounds of the invention have been found to exhibit antifungal activity, and they are consequently useful as active ingredients in fungicidal compositions.

The present invention therefore also embraces fungicidal compositions containing the novel compounds of the invention as active components. Alternatively, the active ingredient of the fungicidal composition of the invention may be a fungus of a species belonging to the genus Penicillium capable of producing a compound of the invention, especially the *P. verruculosum* (CMI CC No. 352119) or a mutant thereof capable of producing a compound of the invention. Also a fungal part, e.g. the mycelium, spores, and fruiting bodies containing or capable of producing a compound of the invention may be used as an active ingredient in a fungicidal composition of the invention.

The invention contemplates the use of any of these active ingredients used alone or in combination with any other of the compounds of the invention or any other biologically active or biocidal agent or plant growth regulator as active components in a fungicidal composition.

A fungicidal composition according to the invention having a fungicidally active compound of the invention as its active ingredient may for agronomical and/or horticultural applications be formulated by mixing the active principle with suitable inert and compatible carriers or diluents to obtain a composition of the type generally used in agricultural compositions, examples of which are further discussed below.

The diluent or carrier in the composition of the invention may be a solid or a liquid conventionally used for the purpose. As solid carriers bentonite diatomaceous earth, apatite, gypsum, talc, pyrophyllite, vermiculite, ground shells, and clay may be mentioned.

In order to obtain a homogeneous and/or stable formulation, a surface-active agent may be associated with the diluent or carrier. The surface-active agent may, for instance, be a dispersing agent, an emulsifying agent or a wetting agent, examples of which are anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Non-ionic agents include condensation products of fatty acid esters, fatty alcohols, fatty acid amides or fatty-alkyl-of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxxide, acetylenic glycols such as 2,4,7,9-tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The composition of the invention can be in any form known in the art for the formulation of agrochemicals, for example, an emulsifiable concentrate, a concentrated emulsion, an aqueous emulsion, a solution, a dispersion, a suspension concentrate, a release formulation (including a slow release formulation), a seed dressing, a granular formulation, a water soluble powder, a wettable powder, a dusting powder, a dispersible powder, an alginate, a xanthan gum and/or an aerosol. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent. Another suitable concentrate is a flowable suspension concentrate which is formed by grinding the active ingredient with water or other liquid, a wetting agent and a suspending agent.

A dusting powder comprises the active ingredient intimately mixed and ground with a solid pulverulent diluent, for example, kaolin. A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit. Wettable powders, granules or grains usually comprise the active ingredient in admixture with a suitable surfactant and an inert powder diluent such as china clay.

Depending on the circumstances such as the crop wherein fungi are to be controlled, the environmental conditions or other factors, a composition of the invention in addition to said fungicidally active compounds of the invention may also contain other active ingredients such as other biocides, e.g. fungicides, pesticides, herbicides, insecticides, nematocides or acaricides, or plant nutrients or fertilizers.

Examples of other fungicides which can be combined with the active compounds of the invention include especially ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of non azole EBis include nuarimol, fenarimol, fenpropimorph, tridemorph and fenpropidine.

Further fungicides which can be combined with compounds of the invention include:

Dithiocarbamates, e.g. thiram, maneb, zineb and mancozeb;
Phatalimides, e.g. captan, folpet and captafol;
Carboxines, e.g. carboxin and oxycarboxin;
Benzimidazoles, e.g. benomyl, carbendazim and fuberidazole;
Carbamates, e.g. prothiocarb and propamocarb;
Isoxazoles, e.g. hymexazol;
Cyanoacetamides, e.g. cymoxanil;
Ethylphosphonates, e.g. fosetylaluminium;
Phenylamides, e.g. furalaxyl, metalaxyl, benalaxyl, ofurace, cyprofuram and oxandixyl;
Dicarboximides, e.g. procymidone, iprodione and vinclozolin;
Organophosphorous fungicides, e.g. pyrazophos, triamiphos, ditalimfos and tolcofosmethyl; and
Aromatic hydrocarbon fungicides, e.g. quintozene, dichloren, and diphenyl.

The concentration of the active compounds of the invention described herein in the compositions of the invention may vary within a wide range depending on the type of formulation and the field of application.

In order to provide the antifungal composition of the invention with a satisfactory antifungal activity, the active compound should normally be present in an amount of from 0.001 µg/ml to 100 mg/ml, such as from 0.05 µg/ml to 10 mg/ml, especially from 0.1 µg/ml to 5 mg/ml.

The concentration of the fungicidally active compounds of the invention in the compositions of the present invention when used alone or in combination with a conventional fungicide, as applied to plants is preferably within the range from about 0.001 to about 30 percent by weight, especially 0.01 to 3.0 percent by weight, although it may vary more widely and be, for instance, within the range from about 5 to about 95 percent by weight of the composition.

The concentration of the other fungicidally active ingredient in the mixed composition of the present invention, as applied to plants is preferably within the range of 0.001 to 50 percent by weight, especially 0.01 to 10 percent by weight, although it can vary widely and can be, for example, from 5 to 80 percent by weight of the composition.

In a further aspect the invention relates to a method of controlling fungi at a locus infested or liable to be infested therewith, which comprises applying to said locus a compound or a fungicidal composition of the invention as defined above.

Compounds of the invention have been found to be particularly potent towards fungi belonging to the class of Ascomycetes, Oomycetes, Bacidiomycetes or Deuteromycetes and accordingly, the locus to be treated with the fungicidal composition is one infected or liable to be infected with such fungi. Typically, the locus is selected from the group consisting of plants, timber, wood, cosmetics, feeds and foods.

Examples of fungal genera and species which has either been found to or is expected to be sensitive to compounds of the invention are fungi of the genera Pyrenophora, especially the species *Pyrenophora teres* and *Pyrenophora graminea*, Phoma, especially the species *Phoma lingam* or *Phoma betae*, Sclerotinia, especially the species *Sclerotinia sclerotiorum*, Monilinia, especially the species *Monilinia fructigena*, Botrytis, especially the species *Botrytis cinerea*, Ascochyta, especially the species *Ascochyta pisi*, Alternaria, especially the species *Alternaria alternata*, and Venturia, especially the species *Venturia inequalis*.

In connection with the method of the invention for controlling fungi, the fungicidal composition may for agronomical or horticultural uses be applied to a region to be treated either directly to the soil as a pre-emergence treatment or to the foliage or fruits of the plants as a pre- and/or post-emergence treatment. Depending on the crop and circumstances the treatment may be postponed until seeds or fruits appear on the plants, wherein fungi are to be controlled. Sometimes, it is practicable to treat the roots of a plant before or during planting, for example by dipping the roots in a suitable liquid or solid composition.

The active preparation or the compositions of the invention can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. When the active preparation of the invention is applied directly to the plant a suitable rate of application is from 0.001 to 50 kg per hectare, preferably from 0.05 to 5 kg per hectare.

In the method of the invention the active preparation of the invention alone or in combination with a conventional biocide can also be applied to seeds or other habitats. Thus the preparation can be applied directly to the soil before, at or after drilling so that the presence of active ingredient in the soil can control the growth of fungi which may attack seeds.

The compositions may be applied in amounts corresponding to from about 1 g to about 50 kg fungicidally active compound per hectare.

When the soil is treated directly the active preparation alone or in a mixture with the conventional biocide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.01 to 50 kg per hectare, more preferably from 0.05 to 5 kg per hectare.

Although the present invention has been described in detail in connection with controlling fungi in plants, it is also anticipated that the fungicidally active compounds of the invention may be used for controlling fungi in mammals, including humans; for the preservation of wood by adding said compounds to wood preservation and/or impregnation compositions; for the preservation of food or feed by adding the compounds directly to the food or feed or to the containers in which it is present; and for the preservation of cosmetics. Also, the active compounds of the invention may be useful as a fungicide and preservant in paints—both to prevent growth in the paint during storage, and growth on the painted object such as the plastered surface of a house—and as an additive to growth media, e.g. for cultivation of bacteria or yeast.

The present invention is further illustrated in the following examples which are not intended, in any way, to limit the scope of the invention as claimed. Various modifications of the invention in addition to those shown and described herein will from the foregoing description be apparent to those skilled in the art. Such modifications are intended to fall within the scope of the appended claims.

MATERIALS AND METHODS

DEPOSITION OF MICROORGANISMS

For the purpose of describing this invention in detail a strain of the fungus *Penicillium verruculosum* (IMI CC No. 352119) has been deposited with the International Mycological Institute Culture Collection (IMI CC), Ferry Lane, Kew, Surrey TW9 3AF, England, for the purposes of patent procedure on the date indicated below. IMI CC being an international depository under the Budapest Treaty affords permanence of the deposit in accordance with rule 9 of said treaty.

| Deposit date: | 9 April, 1992 |
|---|---|
| Depositor's ref.: | 33-851 |
| IMI CC designation: | IMI CC No. 352119 |

The strain IMI CC No. 352119 belongs to the class Deuteromycete, subclass Hyphomycetidae and family Moniliaceae.

OTHER PRODUCERS OF THE COMPOUND 1A

By screening of various isolates of all species in Penicillium subgenus Biverticillium and the closely related teleomorphic state Talaromyces (C. R. Benjamin) according to the method of Frisvad and Thrane (1987) the following strains were found to be producers of Compound Ia:

FRR 635 (=IMI 68239=CBS 312.59=ATCC 18315=IFO 5728), ex. type of *P. aculeatum* var. *apiculatum* (Abe) CBS 548.73 and CBS 264.67 (both allocated to *P. aculeatum* by CBS before the two species were synomised by Stolk and Samson (1983)), and CBS 583.72B (*T. ucrainicus*, Udagawa) the only strain in Talaromyces found to produce the compound.

Cultivation of the strain

The fungus may be grown on agar slants containing the following ingredients in grams/liter:

| | |
|---|---|
| yeast extract | 4.0 |
| potassium dihydron phosphate | 1.0 |
| magnesium sulphate heptahydrate | 0.1 |
| glucose | 15 |
| Bacto (Difco Lab., Detroit, USA) agar | 20 |

The substrate, termed YPG agar, is autoclaved at 121° C. for 20 or 40 minutes. Slants containing 12 ml of YPG agar were inoculated with spores of the strain identified by IMI CC 352119 and subsequently incubated at 20°–25° C. for 7 days or longer.

Fungicide production

Compounds of formula I and II, namely compounds having the formula Ia, Ib and IIa, may be produced in Erlenmeyer flasks containing 100 ml of a medium consisting of the following ingredients: yeast extract 2%, sucrose 15%, $CuSO_4$ 5 ppm, $ZnSO_4$ 10 ppm, agar 2% and demineralized water. The substrate is sterilized by autoclaving at 121° C. for 40 minutes. Each flask is inoculated with a drop of spores of IMI CC 352119. The stationary flasks are incubated at 25° C. for 7–14 days and, subsequently, the active compound is extracted with an organic solvent, e.g. ethanol, methanol, ethylacetate or acetone.

Extraction

To each flask 200 ml of methanol are added and the flasks are shaken at 18° C. overnight. The mycelium and unused substrate are removed by centrifugation and the supernatant is analyzed for fungicidal activity.

Submerged cultivation

The fungicide can also be produced in submerged cultures in media containing other sources of carbon and nitrogen assimilable by the microorganism and generally low levels of inorganic salts. In addition, the media may be supplemented with trace metals. A specific substrate for submerged fermentation may be prepared by mixing 20 g of yeast extract (Difco), 150 g of sucrose, 1 ml of trace metal solution (8.9 g $ZnSO_4 \times 7H_2O$ and 3.9 g $CuSO_4 \times 5H_2O$ dissolved in 500 ml distilled water) and adding distilled water to 1 L. The pH is adjusted to 6.4 using 4M HCl and the substrate is autoclaved at 121° C. for 20 minutes. Each Erlenmeyer flask (500 ml) containing 100 ml substrate is inoculated with approx. $10^6$ spores from a YPG-1 agar slant. The flasks are shaken (230 rpm) for 7 days at 25° C.

The mycelium is separated by centrifugation and extracted with ethanol (100 ml per flask).

EXAMPLES

Example 1

Fermentation

A 500 ml Erlenmeyer flask with 100 ml of substrate prepared as described above (in "Fungicide production") was inoculated with approx $10^6$ spores from an YPG agar slant previously inoculated with *P. verruculosum* IMI CC No 352119. The flasks were shaken at 230 rpm at 25° C. for 3–14 days whereafter the supernatant was separated by centrifugation and the active ingredient was extracted from the residue with 100 ml of methanol as described above.

Example 2

Isolation and Characterization of Compounds Ia, IIa and Ib

The methanolic extract from 20 fermentation flasks was concentrated under reduced pressure to 50 ml. After addition of 200 ml of water, the aqueous phase was extracted thrice with 100 ml portions of ethylacetate. The organic phase was placed in a freezer at −18° C. over night and the separated ice removed by filtration. Evaporation to dryness yielded 2 g of the crude extract.

This primary extract was subjected to reversed phase HPLC (LiChroprep RP18 15–25 µm, 20×230 mm, gradient of aqueous methanol 10 ml/min, detected by UV absorption at 225 nm) to yield three fractions: Fraction I (45 mg) mixture of compounds Ia(90%)+IIa(10%), Fraction II (216 mg) mixture of compounds Ia(50%)+IIa(50%), Fraction III (28 mg) compound Ib. Rechromatography of fraction III in the same system yielded pure Ib (18 mg) as an amorphous glass. The compounds Ia and IIa were purified to homogeneity by further reversed HPLC (LiChroPreP RP18 7 µm, 10×250 mm eluted with a gradient of aqueous MeOH, 4 ml/min, detected by UV absorption at 225 nm), both obtained as amorphous powders, Ia (128 mg) and IIa (52 mg).

The compounds have the following physical and spectroscopic characteristics:

Compound Ia
Appearance: Pale yellowish powder
Molecular comp.: $C_{32}H_{38}O_{15}$
UV ($\lambda nm(\epsilon)$): 303(10,200), 265(22,600), 217(41,000)
$[\alpha]_D$ (c=1.0,MeOH): −22°

| $^1$H-NMR: | TABLE 1 |
|---|---|
| $^{13}$C-NMR: | 171.26(s), 170.91(s), 170.59(s), |
| | 170.32(s), 170.16(s), 166.17(s), |
| | 165.85(s), 163.26(s), 163.20(s), |
| | 143.34(s), 143.20(s), 113.60(d), |
| | 112.77(d), 106.03(s), 105.54(s), |
| | 102.81(d), 102.65(d), 73.35(d), |
| | 72.49(d), 72.27(d), 69.95(d), 69.90(d), |
| | 63.23(t), 42.59(t), 41.64(t), 40.92(t), |
| | 40.51(t), 36.36(t), 20.11(q), 20.05(q), |
| | 19.57(q), 19.40(q) |

Compound IIa
Appearance: Pale yellowish powder
Molecular comp.: $C_{32}H_{38}O_{15}$
UV ($\lambda nm(\epsilon)$): 303(9,000), 265(20,100), 217(39,200)
$[\alpha]_D$ (c=0.8,MeOH): −5°

| $^1$H-NMR: | TABLE 1 |
|---|---|
| $^{13}$C-NMR: | 171.37(s), 170.32(s), 171.06(s), |
| | 170.70(s), 170.50(s), 166.07(s), |
| | 165.48(s), 163.20(s), 163.03(s), |
| | 143.52(s), 143.38(s), 112.74(d), |
| | 112.14(d), 106.32(s), 105.82(s), |
| | 102.50(d), 102.49(d), 72.83(d), |
| | 72.66(d), 70.23(d), 70.00(d), 68.22(t), |
| | 66.71(d), 41.72(t), 41.39(t), 40.94(t), |
| | 40.67(t), 39.89(t), 20.03(2C,q), |
| | 19.80(q), 19.66(q) |

Compound Ib
Appearance: Pale yellow glass
Molecular comp.: $C_{32}H_{38}O_{14}$
UV ($\lambda nm(\epsilon)$): 303(10,100), 265(22,200), 217(43,000)
$[\alpha]_D$ (c=0.4,MeOH): −21°

| $^1$H-NMR: | TABLE 1 |
|---|---|
| $^{13}$C-NMR: | 171.26(s), 170.99(s), 171.27(s), |
| | 170.14(s), 170.11(s), 166.22(s), |
| | 165.94(s), 163.35(s), 163.29(s), |
| | 143.30(s), 143.23(s), 113.55(d), |
| | 112.85(d), 105.99(s), 105.57(s), |

-continued 102.84(d), 102.70(d), 73.30(d),
72.47(d), 70.23(d), 69.98(d), 69.94(t),
68.41(d), 42.59(t), 41.73(t), 41.01(t),
40.97(t), 40.63(t), 20.14(q), 20.00(q),
19.89(q), 19.54(q), 19.49(q)

TABLE 1

$^1$H-NMR data in acetone-$d_6$ for compounds Ia, Ib and IIa. δ-values in ppm relative to internal TMS, J-values in Hz.

|  | Compound Ia δ (m, J) | Compound IIa δ (m, J) | Compound Ib δ (m, J) |
|---|---|---|---|
| H—C(4) | 6.29(d, 2.5) | 6.30(d, 2.5) | 6.29(d, 2.5) |
| H—C(6) | 6.37(d, 2.5) | 6.38(d, 2.5) | 6.37(d, 2.5) |
| H$_2$—C(8) | 3.47(dd, 7/13) | 3.58(dd, 7/13) | 3.50 (dd, 7/13) |
|  | 2.99(dd, 8/13) | 2.90(dd, 7/13) | 2.96(dd, 8/13) |
| H—C(9) | 5.02(m) | 5.04(m) | 5.02(m) |
| H$_3$—C(10) | 1.19(d, 6) | 1.18(d, 6) | 1.19(d, 6) |
| H$_2$—C(12) | 2.76(AB) | 2.55(dd, 5/16) | 2.64(d, 7) |
|  |  | 2.46(dd, 8/16) |  |
| H—C(13) | 5.29(seks, 5) | 4.23(m) | 5.28(seks, 6) |
| H$_{2/3}$—C(14) | 3.66(d, 5) | 4.20(dd, 5/11) | 1.28(d, 6) |
|  |  | 4.06(dd, 5/11) |  |
| H$_2$—C(16) | 2.79(nd)* | 2.96(dd, 8/16) | 2.91(dd, 7/16) |
|  | 2.90(nd)* | 2.84(dd, 5/16) | 2.74(dd, 7/16) |
| H—C(17) | 5.55(seks, 6) | 5.58(m) | 5.54(seks, —) |
| H$_3$—C(18) | 1.45(d, 6) | 1.48(d, 6) | 1.45(d, 6) |
| H—C(22) | 6.30(d, 2.5) | 6.29(d, 2.5) | 6.31(d, 2.5) |
| H—C(24) | 6.36(d, 2.5) | 6.37(d, 2.5) | 6.35(d, 2.5) |
| H$_2$—C(26) | 3.58(dd, 6/13) | 3.41(dd, 7/13) | 3.60(dd, 6/13) |
|  | 2.79(nd)* | 3.10(dd, 8/13) | 2.78(dd, 9/13) |
| H—C(27) | 5.02(m) | 5.15(seks, 7) | 5.03(m) |
| H$_3$—C(28) | 1.15(d, 6) | 1.24(d, 6) | 1.13(d, 6) |
| H$_2$—C(30) | 2.77(nd)* | 2.95(dd, 6/16) | 2.92(dd, 6/16) |
|  | 2.89(nd)* | 2.78(dd, 8/16) | 2.72(dd, 7/16) |
| H—C(31) | 5.55(seks, 6) | 5.53(m) | 5.55(m) |
| H$_3$-(32) | 1.46(d, 6) | 1.44(d, 6) | 1.44(d, 6) |

*nd = not determined

Example 3

Acetylation of Ia (→Formula I: R=COCH$_3$, R$^1$=OCOCH$_3$)

3.6 mg of compound Ia obtained as described in Example 2 above were dissolved in 0.5 ml of pyridine and 0.3 ml of acetic anhydride was added under cooling in an ice bath. The resulting mixture was allowed to stand for two hours at room temperature, and subsequently excess reagent was destroyed by the addition of 1 ml of crushed ice and acidification with 4M sulfuric acid. After stirring for 10 minutes, the mixture was extracted twice with 2 ml portions of dichloromethane. The combined extracts were washed with 2×1ml 2M H$_2$SO$_4$, 1 ml H$_2$O and 1 ml saturated aqueous NaHCO$_3$ and dried (Na$_2$SO$_4$). The solvent was evaporated and the product purified by preparative TLC (Merck silica, 20×20 cm) using chloroform-MeOH (50:1) as eluent, to give 2.1 mg of the pentaacetate as an amorphous solid, LSIMS 873 (MH$^+$). $^1$H-NMR (δ, multiplicity,J Hz) in CDCl$_3$, δ$_{CDCl_3}$=7.27 ppm: 6.93 (1H,d,2.2), 6.90 (1H,d,2.2), 6.88 (1H,d,2.2), 6.84 (1H, d,2.2), 5.55 (2H,m), 5.47 (1H,m), 5.02 (1H,m), 4.95 (1H,m), 4.37 (1H,dd,4/12), 4.08 (1H,dd,5/12), 3.07 (1H,dd,5/14), 2.96 (1H,dd,7/16), 2.95 (1H,dd,8/15), 2.75 (1H,dd,8/17), 2.70 (1H,dd,8/16), 2.62 (2H,d,7), 2.58 (1H,dd,8/13), 2.56 (1H,dd, 4/16), 2.55 (1H,dd,4/16), 2.29 (3H,s), 2.26 (3H,s), 2.25 (2×3H,s), 2.24 (3H,s), 2.05 (3H,s), 1.39 (3H,d,6.2), 1.38 (3H,d,6.2), 1.28 (3H,d,6.2), 1.06 (3H,d,6.2).

Acetylation of Compound IIa (→Formula II: R=R$^1$=COCH$_3$)

5.0 mg of compound IIa obtained as described in Example 2 above were acetylated as described above for the compound Ia. After preparative TLC 4.1 mg of product were obtained. LSIMS 873 (MH$^+$). $^1$H-NMR in CDCl$_3$ (conditions as above): 6.94(d,1H,2.2), 6.88–6.90 (3H,3× d's), 5.58 (1H,m), 5.55 (1H,m), 5.34 (1H,m), 5.10 (1H,m), 5.09 (1H,m), 4.35 (1H,dd,4.0/12), 4.09 (1H,dd,5.–6/12), 3.07 (1H,dd,8/14), 3.06 (1H,dd,7/14), 2.90 (1H,dd,6/14), 2.85 (1H,dd,6/14), 2.79 (1H,dd,7/16), 2.78 (1H,dd,8/16), 2.61 (1H,nd), 2.60 (2H,d,6.5), 2.57 (1H,not determined), 2.28 (2×3H, s), 2.26 (3H,s), 2.25 (3H,s), 2.01 (3H,s), 1.41 (3H,d,6.3), 1.41 (3H,d,6.3), 1.24 (3H,d,6.3), 1.18 (3H,d,6.2).

Example 4

Fungicidal activity

In vitro

The purpose of this example is to demonstrate the activity spectra of the purified compounds Ia, IIa and Ib obtained as described in Example 2.

The following pathogens were used:

*Pyrenophora teres* (Pt) net blotch disease

*Phoma lingam* (Pl) canker and dry rot

*Phoma betae* (Pb) seedling black rot, black leg

*Sclerotinia sclerotiorum* (Ss) white mould disease, stem rot

*Monilinia fructigena* (Mf) brown rot, fruit rot

*Botrytis cinerea* (Bc) grey mould

*Ascochyta pisi* (Ap) leaf, stem and pod rot

*Alternaria alternata* (Aa) black mould coverings, leaf spot

*Venturia inequalis* (Vi) Apple scab.

Each of the above mentioned 9 pathogens were separately innoculated into 100 ml of potato dextrose (PD) bouillon and shaken at 200 rpm at 25° C. for 7 days. The mycelium was harvested and homogenized for about 10 seconds in a Warring blender and 1–5 ml of the blended mycelium was transferred to petri dishes with a diameter of 14 cm. The amount of mycelium transferred varied because the fungi did not produce equal amounts of mycelium in the shake flasks. 20 ml of potato dextrose agar (PDA) having a temperature of 45° C. were poured into each of the petri dishes and thorougly mixed with the blended mycelium present therein. When the agar had solidified, wells of a diameter of 4 mm were punched in the agar, and 15 µl of test solutions containing varicus concentrations of compound Ia, Ib and IIa dissolved in ethanol was applied to each well. The plates were incubated for three days at 25° C. and the inhibition zones measured (in mm).

The experiments were repeated and in the second run, Bc plates were made from Bc spores (the plates were termed Bc2) as such plates may result in a more uniform growth.

Results

TABLE 2

| Compound | Conc. mg/ml | Bc1 | Bc2 | Pt | Pb | Ap | Pl | Aa | Ss | Mf |
|---|---|---|---|---|---|---|---|---|---|---|
| Ia | 1.0 | + | 56d | 40d | 0 | 0 | 49d | 0 | 50d | 50v |
| Ia | 0.5 | + | 48d | 35d | 0 | 0 | 42d | 0 | 42d | 45v |
| IIa | 0.1 | + | 30d | + | 0 | 0 | 31d | 0 | 40d | 40v |
| Ia | 0.05 | + | 12d | + | 0 | 0 | 18d | 0 | 24d | 34v |
| Ia | 0.01 | 0 | – | 0 | 0 | 0 | 0 | 0 | 0 | 20v |
| IIa | 1.0 | + | 45d | 0 | 0 | 0 | 18d | 0 | + | 40v |
| IIa | 0.5 | + | 37d | 0 | 0 | 0 | 14d | 0 | + | 40v |
| IIIa | 0.1 | 0 | 0 | 0 | 0 | 0 | 0 | 0 | 0 | 0 |
| Ib | 1.0 | 0 | 30d | 33d | 20d | 15v | 12d | 17c | 0 | 25v |
| Ib | 0.5 | 0 | 26d | 17d | 17d | + | + | 15c | 0 | 0 |
| Ib | 0.1 | 0 | 0 | 0 | 0 | 0 | 0 | 0 | 0 | 0 | c = clear;
d = diffuse;
v = very diffuse;
+ = very weak

The Bc zones obtained for Ia and IIa were very diffuse and could be seen only after 3 days of incubation. When tested for compound of formula Ib, however, clearing zones could be observed after 2 days. These clearing zones were unusual in being very clear, indicating a different mode of action of compound of formula Ib as compared to compounds of formula Ia and IIa.

From the table above it is evident that compounds of formula Ia and IIa have similar activity spectra, although the compound of formula Ia was more effective than the compound of formula IIa. Each of these compounds was active against 5 pathogens (with respect to Bc only for the plate containing spores).

The compound of formula Ib is seen to have a very broad activity spectrum, in that it is active, to a higher or lower degree, towards all of the pathogens tested.

Example 5

Fungicidal Activity in vivo

Activity of the compounds Ia and Ib against *Botrytis cinerea*

Host: *Lycopersicon esculentum* (tomato, var. First in Field)

Potato plants (5 weeks old) were sprayed to run off with liquid solutions using a handhold sprayer (Bink Bullows 900). The solution (70% EtOH) had different concentrations of the compounds Ia and Ib. The plants were kept 24 hours in a green house to dry before they were inoculated with a spore suspension containing $1 \times 10^5$ spores/ml in 25% grape juice. The inoculation was carried out with a handhold atomizer (Wagner, Pico Bel). The plants were then incubated (16 hours light (1000 lux) and 8 hours dark) at 15°–20° C. in clear polyethylene bags to raise the relative humidity to 95–100%.

After 6 days the assessment was done. The results are shown below:

| Compound Ia | |
|---|---|
| 1000 ppm | approx. 60% protection |
| 375 ppm | approx. 60% protection |
| 37 ppm | approx. 10% protection |
| Compound Ib | |
| 360 ppm | approx. 50% protection |
| 36 ppm | approx. 50% protection |

Example 6

Cytotoxic Properties of Compounds IA, IB and IIA

The cytotoxic properties of IA, IB and IIA were determined in a mouse peritoneal macrophage assay and showed $IC_{50}$ values for cellular ATP (viability) and chemiluminescence (phagocytosis) to be:

Compound IA: 2.5 and 2.0 µg/ml;

Compound IB: 6 and 6 µg/ml; and

Compound IIA: both less than 10 µg/ml.

REFERENCES CITED IN THE SPECIFICATION

Alexander Steinbüchel: Nachr. Chem. Tech. Lab. 39 (1991), 1112;

Seebach, Dieter; Brändli, Urs; Schnurrenberger, Peter; Przybylski, Michael: Helvetica Chimica Acta, 71 , 155 (1988);

Fuska, J.; Nemec, P. and Kuhr, I.: *J. Antibiot.*, 25, 208 (1972);

Sedmera, P.; Vokoun, J.; Podojil, M.; Vaněk, Z.; Fusca, J.; Nemec, P and Kuhr, I.: *Tetrahedron Letters*, 1347 (1973);

Boeckman, R. K., Jr.; Fayos, J. and Clardy, J.: *J. Am. Chem. Soc*, 96, 5954 (1974);

Worthington, P. A. *Natural Product Reports*, p.47 (1988);

Seuring and Seebach, Liebigs Ann. Chem. 1978, 2044–2073);

Ito, M.; Tsuchida, Y.; Mizoue, K. & Hanada, K.: NG-011 and NG-012, Novel Potentioators of Nerve growth Factor II. The structure Determination of NG-011 and NG-012. J. Antibiotics 45, 1566 (1992);

Stolk, A. C. & Samson, R. A.: The ascomycete genus Eupenicillium and related Penicillium anamorphs. Stud. Mycol. (Baarn) 23, 1–149 (1983);

Frisvad, J. C. & Thrane, U.: Standardized high-performance liquid chromatography of 182 mycotoxins and other fungal metabolites based on alkylphenone retention indices and UV-VIS spectra (diode array detection). J. Chromatography 404, 195 (1987).

We claim:
1. A compound having the general formula I

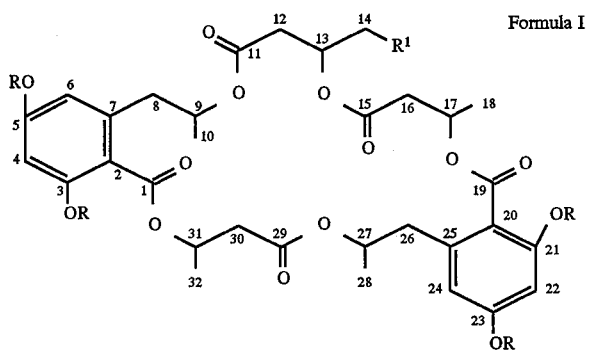

wherein
- $R^1$ is hydrogen, hydroxy, —$OR^2$, or —$OCOR^3$, in which
- $R^2$ is straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group; and
- $R^3$ is straight or branched alkyl with 1–10 carbon atoms, straight or branched alkenyl with 2–10 carbon atoms, straight or branched alkynyl with 2–10 carbon atoms, or aryl, optionally mono- or plurisubstituted with straight or branched alkyl with 1–10 carbon atoms, hydroxy, alkoxy, halogen, an amino or a nitro group; and
- R is hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group, or —$COR^3$ in which $R^3$ is as defined above; with the exception of the compounds where $R^1$ is hydrogen or hydroxy and R is hydrogen.

2. The compound according to claim 1, wherein $R^1$ is hydrogen or hydroxy and/or R is methyl or wherein $R^1$ is hydrogen, hydroxy or $OCOCH_3$ and R is $COCH_3$.

3. A compound having the general formula II

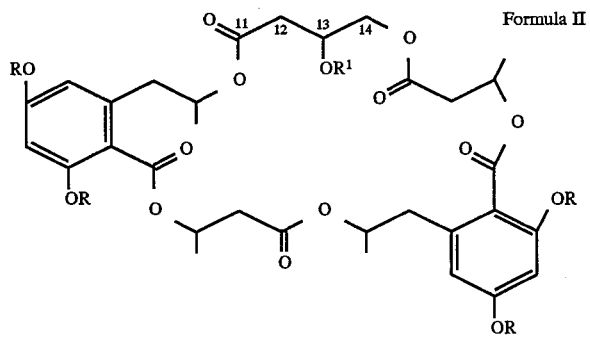

wherein R and $R^1$ independently are hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group, or —$COR^3$ where $R^3$ is as defined in claim 1.

4. The compound according to claim 3, wherein R is hydrogen, methyl or —$COCH_3$ or $R^1$ is hydrogen or —$COCH_3$.

5. The compound II according to claim 4 in which R and $R^1$ are hydrogen.

6. A method of preparing the compound of claim 1 or 3 comprising
   a) cultivating a microorganism capable of producing said compound in or on a suitable nutrient medium and under suitable conditions so as to obtain a biomass comprising the compound, and
   b) recovering the compound from the biomass and/or the culture medium.

7. The method according to claim 6, which further comprises c) chemically modifying the compound obtained in step b).

8. The method according to claim 6, wherein the microorganism is a fungus.

9. The method according to claim 8, wherein the microorganism is a fungus of the genus Penicillium.

10. The method according to claim 8, wherein the microorganism is a fungus of the species Penicillium verruculosum.

11. The method according to claim 10, wherein the microorganism is a strain of P. verruculosum (IMI CC 352119) or mutant thereof capable of producing said compound.

12. A fungicidal composition comprising as an active ingredient the compound of claim 1 or 3.

13. The fungicidal composition of claim 12, wherein said compound is present in an amount of from 0.001 ug/ml to 100 mg/ml.

14. A fungicidal composition comprising as an active ingredient the compound of claim 1 or 3 and one or more further fungicidal or pesticidal agents and/or growth regulators.

15. The fungicidal composition of claim 14 in which the further fungicidal or pesticidal agents are present in an amount of 0.001 to 50% by weight.

16. The fungicidal composition of claim 14 in which the further fungicidal or pesticidal agents are present in an amount of 0.01 to 10% by weight.

17. A method of controlling fungi at a locus infested with fungi comprising applying to said locus the composition of claim 12 in an amount effective to control said fungus.

18. The method according to claim 17 in which the locus is selected from the group consisting of plants, timber, wood, cosmetics, feeds and foods.

19. The method according to claim 17 in which the fungus to be controlled is a plant pathogenic fungus.

20. The method according to claim 17 in which the fungus to be controlled is a plant pathogenic fungus which belongs to the class selected from the group consisting of Ascomycetes, Oomycetes, Bacidiomycetes and Deuteromycetes.

21. The method according to claim 17 in which the fungus to be controlled is of the genera selected from the group consisting of Pyrenophora, Sclerotinia, Monilinia, Botrytis, Ascochyta, Alternaria, and Venturia.

22. The method according to claim 17 in which the fungus to be controlled is of the species selected from the group consisting of *Pyrenophora teres, Pyrenophora graminea, Phoma lingam, Phoma betae, Sclerotinia sclerotiorum, Monilinia fructigena, Botrytis cinerea, Ascochyta pisi, Alternaria alternata*, and *Ventura inequalis*.

23. A method of preventing fungal infestation at a locus liable to be infested with fungi comprising applying to said locus the composition of claim 12 in an amount effective to prevent infestation of said fungus.

* * * * *